(12) United States Patent
Kumar et al.

(10) Patent No.: US 7,847,127 B2
(45) Date of Patent: Dec. 7, 2010

(54) PROCESS FOR PREPARATION OF ATOVAQUONE AND NOVEL INTERMEDIATES THEREOF

(75) Inventors: Ashok Kumar, Mumbai (IN); Suneel Yeshwant Dike, Maharashtra (IN); Pramil Kumar Mathur, Mumbai (IN); Nellithanath Thankachen Byju, Mumbai (IN); Brajesh Sharma, Mumbai (IN); Swapnil Shreekant Kore, Mumbai (IN); Vitthal Suryabhan Buchude, Mumbai (IN); Dharmendra Singh, Thane (IN)

(73) Assignee: IPCA Laboratories Limited, Mumbai (IN)

( * ) Notice: Subject to any disclaimer, the term of this patent is extended or adjusted under 35 U.S.C. 154(b) by 0 days.

(21) Appl. No.: 12/603,253

(22) Filed: Oct. 21, 2009

(65) Prior Publication Data

US 2010/0081847 A1 Apr. 1, 2010

Related U.S. Application Data

(63) Continuation-in-part of application No. PCT/IN2008/000251, filed on Apr. 17, 2008.

(30) Foreign Application Priority Data

Apr. 19, 2007 (IN) .................. 760/MUM/2007
Feb. 28, 2008 (IN) .................. 408/MUM/2008

(51) Int. Cl.
*C07C 49/603* (2006.01)
*C07C 45/61* (2006.01)
*C07C 45/67* (2006.01)

(52) U.S. Cl. .................. 568/310; 568/314; 568/328

(58) Field of Classification Search .................. 568/310, 568/314, 328
See application file for complete search history.

(56) References Cited

U.S. PATENT DOCUMENTS

| 4,981,874 | A | * | 1/1991 | Latter et al. .................. 514/682 |
| 5,053,432 | A | | 10/1991 | Hudson et al. |
| 6,018,080 | A | | 1/2000 | Dearn |
| 6,649,659 | B1 | | 11/2003 | Dearn |

FOREIGN PATENT DOCUMENTS

| EP | 0362996 A2 | 4/1990 |
| WO | WO-93/11756 A1 | 6/1993 |
| WO | WO-2006/008752 A1 | 1/2006 |

OTHER PUBLICATIONS

Fiser, Louis, et al. "Naphthoguinone Antimalarials. IV-XI. Synthesis.". Journal of American Chemical Society, vol. 70, 3174-3215 (1948).

* cited by examiner

*Primary Examiner*—Sikarl A Witherspoon
(74) *Attorney, Agent, or Firm*—Blank Rome LLP

(57) ABSTRACT

Disclosed herein is a novel process for preparation of atovaquone. The process includes reacting 1,4-naphthoquinone with trans-4-(4-chlorophenyl) cyclohexane carboxylic acid followed by halogenation to obtain a dihalo-compound. Further, dehydrohalogenation of the dihalo-compound produces a monohalogeno-compound which under goes hydrolysis to produce atovaquone. The invention also discloses atovaquone in a substantially pure and well defined polymorphic form designated as "Form IPCA-ATO," and the preparation thereof.

21 Claims, 3 Drawing Sheets

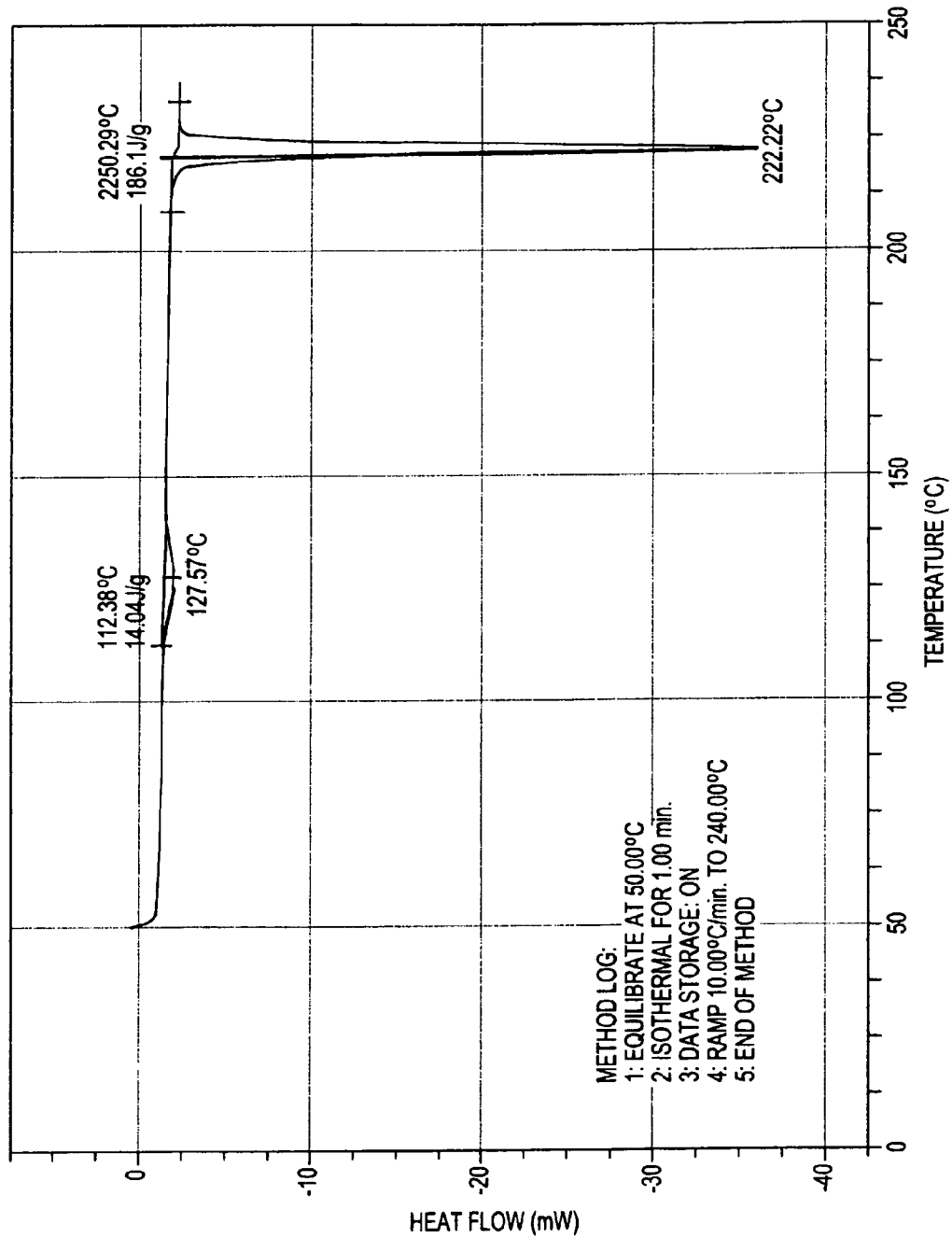

PROCESS FOR PREPARATION OF ATOVAQUONE AND NOVEL INTERMEDIATES THEREOF

This application is a continuation-in-part (CIP) of PCT/IN2008/000251, filed Apr. 17, 2008, which is incorporated herein by reference.

FIELD OF INVENTION

The present invention relates to a new process for preparation of atovaquone. In particular, the present invention relates to novel intermediates useful in the preparation of Atovaquone and obtainment of atovaquone in a novel polymorphic form. More particularly, invention relates to an advantageous crystalline form, that has improved solubility and other bulk characteristics suitable for pharmaceutical application. The present invention also relates to processes for preparing such crystalline form of Atovaquone and its use in industry. atovaquone is a useful medicine for the treatment and prophylaxis of *Pneomcystis carinii* infections.

BACKGROUND OF THE INVENTION

Atovaquone, chemical name being trans-2-[4-(4-chlorophenyl)cyclohexyl]-3-hydroxy-1,4-naphthoquinone, is a hydroxy-1,4-naphtoquinone, an analog of ubiquinone, with antipneumocystic activity. Atovaquone is potently active (in animals and in vitro) against *Pneumocystis carinii*, Plasmodia, and tachyzoite and cyst forms of *Toxoplasma gondii*. Due to its inhibitory effect in sensitive parasites, atovaquone can act by selectively affecting mitochondrial electron transport and parallel processes such as ATP and pyrimidine biosynthesis, thus has got great pharmaceutical interest/importance. Atovaquone is the trans-isomer of 2-[4-(4-chlorophenyl)cyclohexyl]-3-hydroxy-1,4-naphthoquinone whose synthesis, activity and uses are disclosed in the patent Nos. U.S. Pat. No. 5,053,432 ('432 patent) and EP0362996.

There are only a few reports available for the preparation of atovaquone exploring various synthetic alternative. Those report are mainly based on a decarboxylative condensation process, as shown in scheme 1, which is analogous to the method disclosed by Fieser (J. American Chemical Society, vol. 70, 3174-3180 (1948)) yielding the condensation product at only about 1 to 6%. As reported, the production yield of atovaquone using process of the '432 patent is very poor, practically in the range of 3-5%.

Scheme 1.

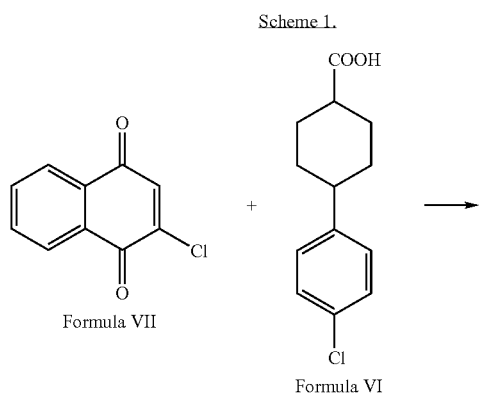

Formula VII

Formula VI

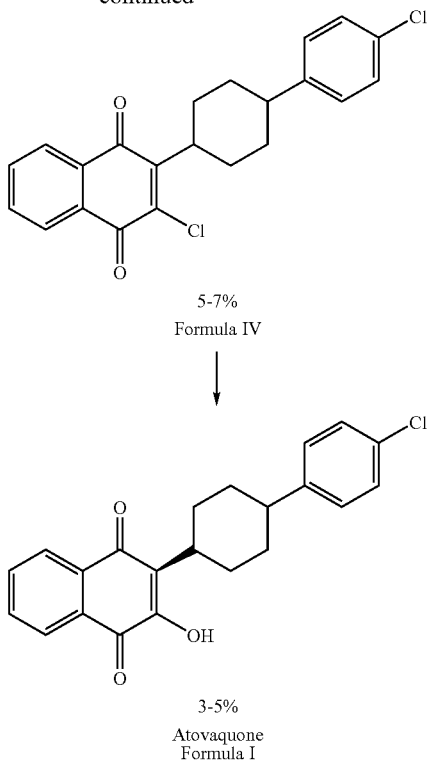

5-7%
Formula IV 3-5%
Atovaquone
Formula I

Thus a search for a manufacturing process for the preparation of Atovaquone resulting in a satisfactory yield/purity of the final product remains undoubtedly of interest.

Apart from this, there is a great challenge in obtaining atovaquone having improved solubility and dissolution characteristics. However, there is only a single publication on the production of different crystalline forms of atovaquone, as disclosed in WO2006008752 ('752 publication). The '752 publication discloses that atovaquone can exist in three different polymorphic forms (designated as Form I, Form II and Form III) and provides analytical characterization for those polymorphs. The product obtained by the basic molecule patent was characterized for the first time in this publication, and designated as Form I. The stability data of the reported forms are not reported. However, it is important to note the reports on micro-particles of atovaquone, for example U.S. Pat. Nos. 6,018,080 and 6,649,659, disclose such micro-particles and processes for producing the same. These patents clearly disclose that the product manufactured by the process of the '432 patent, meaning the crystalline Form I, has poor bioavailability. Microparticles of atovaquone, prepared by a complicated process, have been described to have increased bioavailability. It has been disclosed that the process of U.S. Pat. No. 5,053,432 yields macroparticles of atovaquone that are not suitable to be administered as such, or even by conventional milling, due to poor solubility of the crystals in common organic/aqueous solvents. Therefore, there is a need in the art for new forms of atovaquone, which have improved solubility and bioavailability for making suitable pharmaceutical dosage forms.

Therefore the object of this invention is to develop alternative processes for the synthesis of atovaquone, more specifically in its trans isomer form with improved physical properties.

SUMMARY OF THE INVENTION

The present inventors had discovered that the prior art processes present substantial difficulties in producing Atovaquone in a consistent and reliable manner in satisfactory yields. The invention, therefore, aims to provide a new process for making Atovaquone.

In accordance with one aspect, the invention provides a process for preparation of Atovaquone, which process includes reacting 1,4-naphthoquinone with trans-4-(4-chlorophenyl)cyclohexane carboxylic acid followed by chlorination, dehydrohalogenation, and hydrolysis according to scheme 2.

Optionally, cis and trans isomer of the intermediates separation may be carried in any of the intermediate reaction steps. The intermediate compound of Formula III and substantially pure trans-form of compound of Formula II are novel, and form part of the present invention.

It has been observed that the crystalline forms disclosed in the prior art are substantially coarser crystals and have very poor solubility. It has now surprisingly been found that atovaquone crystals can occur in a structurally different physical form. In another aspect, the present invention provides atovaquone in a novel and substantially pure polymorphic form. The novel polymorph of atovaquone can be obtained as a well defined compound and is herein after designated as "Form

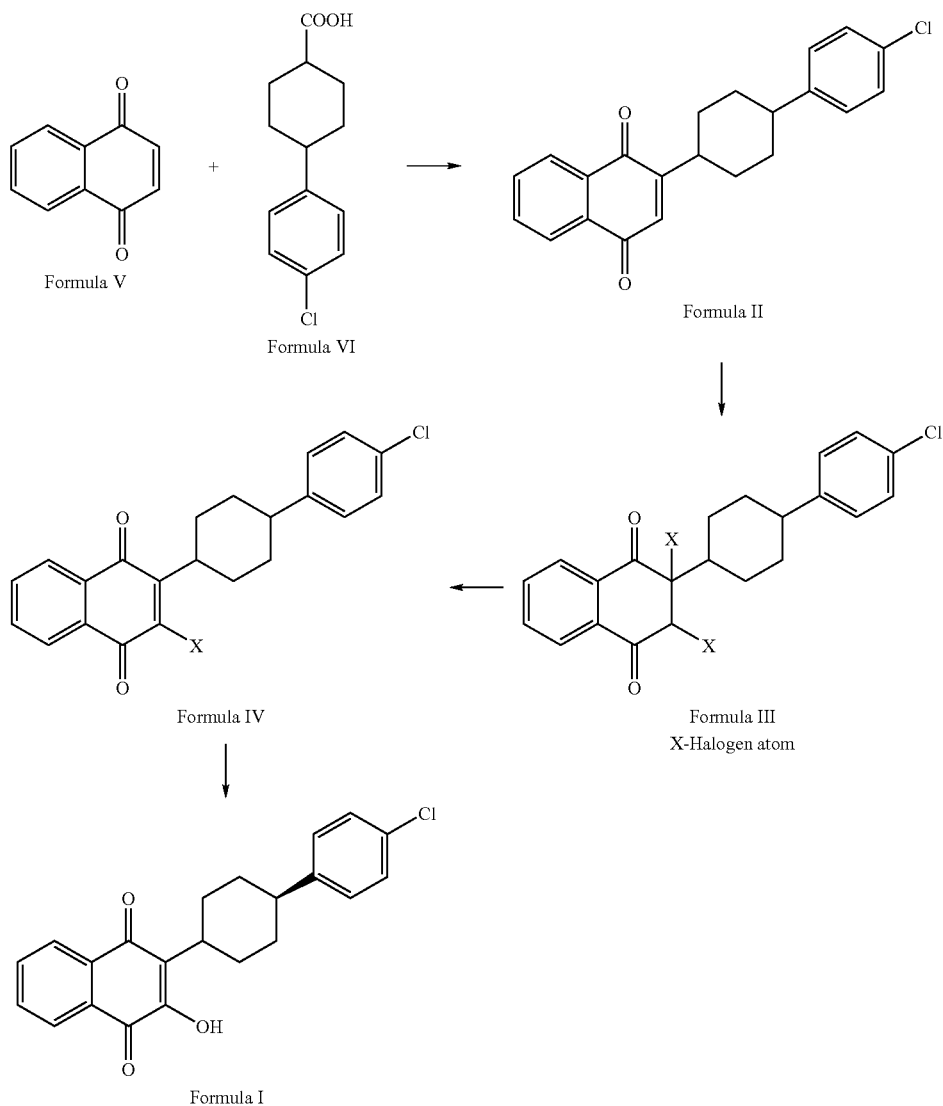

Scheme 2

In one embodiment, intermediate II is isolated in substantially pure trans-form. In another embodiment, the intermediate II obtained as a mixture of its cis and trans-isomers, may be directly subjected to halogenation, dehydrohalogenation, and hydrolysis to obtain an isomeric mixture of atovaquone, followed by epimerization of cis-isomer to trans-isomer.

IPCA-ATO." The character of the new form can be defined either by distinct peaks in X-Ray powder diffraction (XRPD) pattern, distinct endotherms in differential scanning calorimetry (DSC), or peaks in infrared (IR) spectrum.

The present invention also provides suitable processes to obtain and methods for differentiating the novel form of atovaquone (Form IPCA-ATO) from other forms of atovaquone. The compound of the invention is advantageous because it is found to be stable with lower bulk density than the corresponding morphologically different atovaquone compounds of the prior art and is therefore expected to have better solubility properties leading to higher bioavailability. Form IPCA-ATO is also easier to characterize because it exists in a well defined state. Form IPCA-ATO is useful for pharmaceutical application with improved properties/adaptability; and thus, the invention also relates to pharmaceutical compositions containing the compound of the present invention.

BRIEF DESCRIPTION OF THE DRAWINGS

FIG. 3 shows a DSC analysis diagram of an exemplary batch of "Form IPCA-ATO" of atovaquone obtained in accordance with the invention.

DETAILED DESCRIPTION OF THE INVENTION

Figure 1:
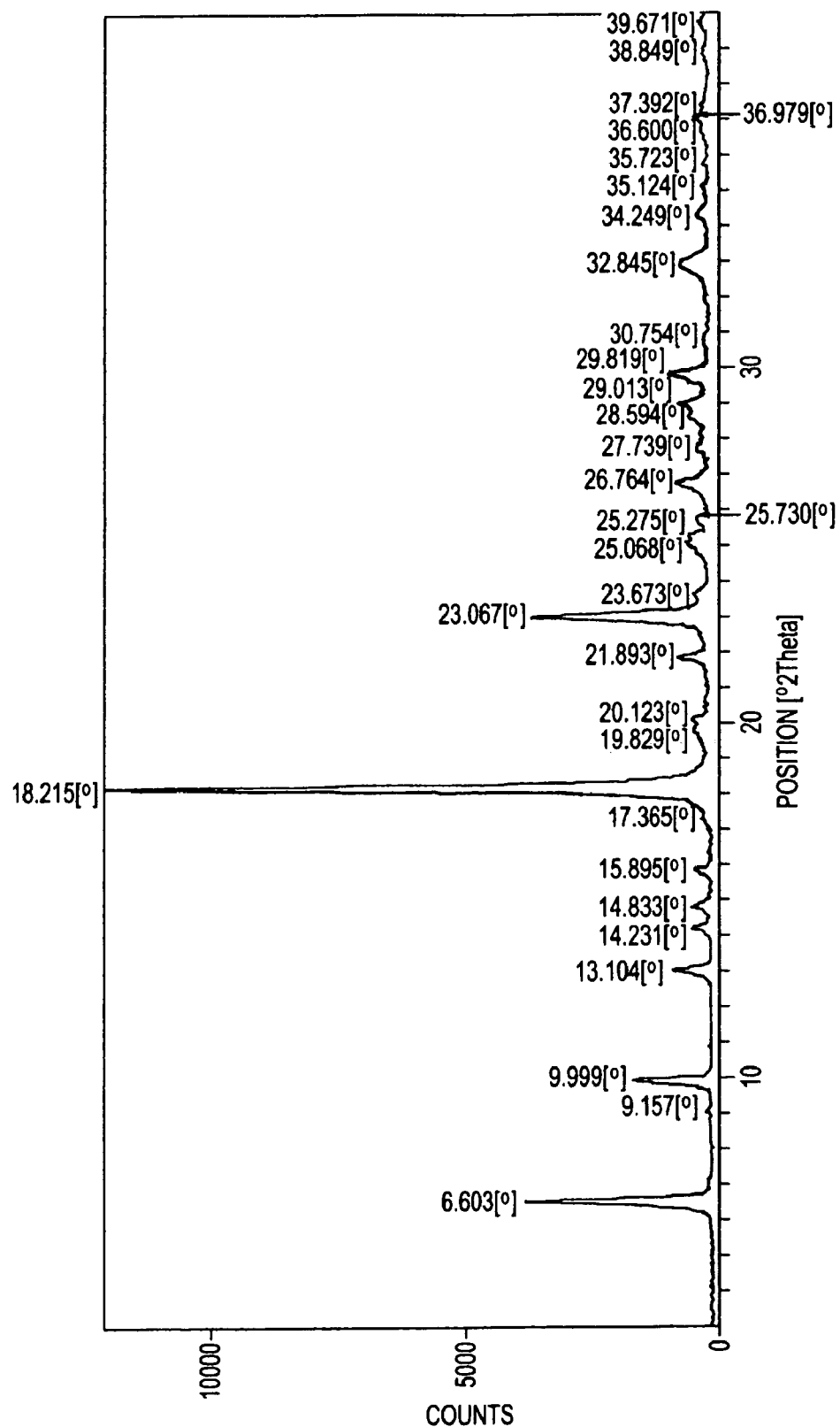
FIG. 1 shows an XRPD of an exemplary batch of "Form IPCA-ATO" of atovaquone obtained in accordance with the invention.

Unless specified otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described. To describe the invention, certain terms are defined herein specifically as follows.

Unless stated to the contrary, any of the words "including," "includes," "comprising," and "comprises" mean "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth in the appended claims.

The term "isolating" is used to indicate separation or collection or recovery of the compound of the invention being isolated in the specified form.

The term "separating from a solvent" with respect to the solids described herein means obtaining a solid of specified characteristics from a solution or a partial solution.

The term "treating" means adding or combining or mixing the stated reagent or materials to the things being treated.

The term "forming a solution" means obtaining a solution of a substance in a solvent in any manner. It encompasses partial solutions.

The term "stable," as used herein, refers to the tendency to remain substantially in the same physical form for at least a month, preferably at least 6 months, more preferably at least a year, still more preferably at least 2 years, when stored under ambient conditions (20° C./60% RH) without external treatment. Substantially the same physical form in this context means that at least 50%, preferably at least 80% and more preferably at least 90% of the crystalline form remains.

For the purposes of this description and claims of the present invention, the phrase "Atovaquone Form IPCA-ATO" refers to the novel form of atovaquone, wherein the "IPCA-ATO," is referring to a crystalline form of atovaquone that one of skilled in the art can identify as a distinct entity distinguishable from other crystalline forms of atovaquone based on the characterization details provided herein.

As used herein, the phrase having "at least one characteristic of Form IPCA-ATO" refers to a crystalline form of atovaquone that possesses at least one of the characteristic PXRD peaks or distinct peaks in IR spectrum provided herein. For example, a single or a combination of PXRD peaks which are not found in other crystalline forms of atovaquone is enough to show at least one of the characteristics of Form IPCA-ATO of atovaquone. A single or a combination of peaks in an Fourier transformed infrared (FT-IR) spectrum provided herein with this invention may also serve the same purpose.

Identification of solids obtained by the present invention can be made by methods known in the art, such as X-Ray powder diffraction, FT-IR spectra. It should be understood that operator, instrument and other similar changes may result in some margin of error with respect to analytical characterization of the solid.

The FTIR, DSC and XRPD methods used for the identification and characterization of the novel form of Atovaquone are described below:

a) FT-IR Spectral Analysis

FTIR spectra of novel form is recorded directly on untreated powder by means of spectrometer. Spectra is recorded at room temperature from 4000 cm$^{-1}$ to 650 cm$^{-1}$, for each sample 32 scans are collected at a resolution of 4 cm$^{-1}$.

b) XRPD Studies.

Analytical characterization of the compound according to the invention is carried out by using X-ray powder diffraction using a PANalytical XpertPRO X-Ray machine made by Philips. The X-ray powder diffraction patterns are recorded with Cu K alpha-1 radiation source (voltage of 45 kV; current: 40 mA). The step scan mode is performed with a step size of 0.008°, at a scan rate of 14.59 step/s.

c) DSC

Differential scanning calorimetry analysis of the novel form is recorded at a heating rate of 10° C. per minute at a temperature range from 50° C. to 250° C.

"Atovaquone" is a free species of trans-2-(4-chlorophenyl)-cyclohexyl)-3-hydroxy-1,4-naphthoquinone, which has the trans geometry. It has the following Formula:

Formula I

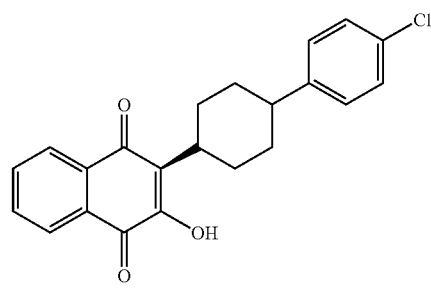

Atovaquone

The inventors of the present invention discovered that the use of 2-chloro-1,4-naphthoquinone (Formula VII) in the condensation reaction with trans-4-(4-chlorophenyl)cyclohexane carboxylic acid (Formula VI) does not provide a reliable, consistent methodology to prepare atovaquone due to poor selectivity; and provides a yield only in the range of 3-5%. The intermediate trans-isomer of compound of Formula IV (scheme 1), according to reported processes, is obtained in only 5-7% yield, and contains a large amount of impurities and the corresponding cis-isomer (Formula IV-cis-geometry) making it difficult to purify. The present inventors, on exploring various process alternatives, for a reliable process solution have found that the use of 2,3-unsubstituted 1,4-naphthoquinone (Formula V) in the condensation reaction provides a significantly better yield in the condensation reaction and also permits reliable isolation of the trans-isomer of Formula II, which may be further converted to atovaquone. The process of the present invention is represented in scheme 2.

Thus, according to the present invention, there is provided a process for preparation of Atovaquone, said process comprises the steps of
  a) reacting 1,4-naphthoquonone (Formula V) with 4-(4-chlorophenyl)cyclohexane carboxylic acid (Formula VI) to obtain the compound of Formula II;
  b) halogenating the compound of Formula II to form a dihalo-compound of Formula III;
  c) subjecting the compound of Formula III to a dehydrohalogenation reaction to obtain a compound of Formula IV; and
  d) converting the monohalogeno-compound of Formula IV into atovaquone or its cis-isomer or a mixture thereof In the process of step (a), 4-(4-chlorophenyl)cyclohexane carboxylic acid (Formula VI) used in the process is preferably in the trans-isomer form. The reaction is conducted in presence of a metal nitrate and a persulphate reagent. Preferably, the metal nitrate is silver nitrate; and the persulphate reagent is ammonium persulphate. The reaction step (a) may be performed in an aqueous and/or organic solvent. The solvent for the reaction can be chosen from any inert solvent, preferably selected from polar protic and polar aprotic solvent. The aqueous solvent is preferably water or water containing organic solvents. More preferably, it is a mixture of water and acetonitrile. The reaction can be carried out optionally in presence of a catalyst, for example, a metal iodide or a phase-transfer catalyst.

The phase transfer catalyst can be, for example, alogen, quaternary ammonium salts substituted with a residue selected from the group consisting of straight or branched chain alkyl group having 1-18 carbon atoms, phenyl lower alkyl group and phenyl group, such as tetrabutylammonium chloride, tetrabutylammonium bromide, tetrabutylammonium fluoride, tetrabutylammonium iodide, tetrabutylammonium hydroxide, tetrabutylammonium hydrogen sulfate, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzylmethyloctadecanylammonium chloride, methyltridecanylammonium chloride, benzyltripropylammonium chloride, benzyltriethylammonium chloride, phenyltriethylammonium chloride, tetraethylammonium chloride, tetramethylammonium chloride and the like; phosphonium salts substituted with a residue selected from the group consisting of straight or branched chain alkyl groups having 1-18 carbon atoms such as tetrabutylphosphonium chloride and the like; and pyridinium salts substituted with a straight or branched chain alkyl group having 1-18 carbon atoms such as 1-dodecanylpyridinium chloride and the like. Among these phase transfer catalysts, quaternary ammonium salts substituted with a straight or branched chain alkyl group having 1-18 carbon atoms, such as tetrabutylammonium bromide or alogen are particularly preferred.

The reaction is carried out usually at a temperature between ambient temperature and the reflux temperature of the solvent, and preferably at a temperature of 50-110° C. The reaction time is usually from about 1 hour to about 10 hours.

It is recommended to use the naphthoquinone (Formula V) in excess, usually in an amount of about 1.1 to 2 mol per mol of the 4-(4-chlorophenyl)cyclohexane carboxylic acid (Formula (VI). Also, the silver nitrate is preferably used in an amount of 0.1 to 0.9 moles, more preferably 0.2 to 0.5 moles per mol of the 4-(4-chlorophenyl)cyclohexane carboxylic acid (Formula VI); and the persulphate reagent is preferably used in an amount of 1.5 to 5 moles, more preferably 1.5 to 2.5 mol per mol of 4-(4-chlorophenyl)cyclohexane carboxylic acid (Formula VI). Optionally, the phase transfer catalyst is preferably used in an amount of 0.1-1 mol, and more preferably 0.1-0.25 mol per mol of the naphthoquinone (Formula V). The metal iodide is preferably used in an amount of 0.1 to 1.0 mole, and more preferably in 0.1 to 0.3 mole per mol of the naphthoquinone (Formula V).

The compound of Formula (II) formed during during step a) can easily be isolated by the conventional separating means. The separating means can be, for example, distillation of solvent and excess reactants followed by crystallization, extraction method using a solvent, dilution method, recrystallization method, column chromatography, preparative thin layer chromatography, etc.

After the completion of step (a), the compound of Formula II is isolated in its cis isomer or trans isomer or as a mixture of its cis and trans isomer. Preferably the product of Formula II is isolated in its trans-form and further used in the step b) conversion process.

In step b), the halogenation reaction of product of Formula II is carried out in presence of a suitable halogenating agent, preferably chlorine. Chlorination is preferably carried out by passing chlorine gas in presence of the compound of Formula II in glacial acetic acid or in any conventional solvent to obtain compound of Formula III as its cis isomer or trans isomer or as a mixture of its cis and trans isomer.

In step c), the dehydrohalogenation of compound III is carried out by treating it with an acid or base in a suitable medium. Preferably, dehydrohalogenation is carried out by treating it with sodium acetate in glacial acetic acid to obtain the compound of Formula IV. The compound of Formula IV can be isolated as its cis isomer or trans isomer or as a mixture of its cis and trans isomer. Preferably, it is isolated as the trans isomer.

The hydrolysis of the compound of Formula IV into the compound of Formula I is carried out by reacting it with a base, such as potassium hydroxide or sodium hydroxide, in a solvent, preferably an alcohol. In case the atovaquone is obtained in its cis isomeric form or in an isomeric a mixture of cis and trans isomer, it is further epimerized to afford the desired trans isomer. The epimerization is conveniently performed by stirring the cis-isomer or a mixture of its cis and trans isomer with sulfuric acid for about 1-6 hours. In an especially preferred process embodiment, the overall procedure may be operated without separation/isolation of isomers and finally epimerizes the undesired cis-isomer to obtain atovaquone in good yields.

The invention provides better yield of the compound of Formula II in the condensation reaction in the order of about 20-22% isolated yield. Thus the yield of the required trans-isomer of the compound of Formula II is improved to a great extent by the practice of the present invention. The isolated compound of Formula II in substantially pure trans-form is not available in literature. With the practice of the present invention, atovaquone yields were improved to 25-30% based on starting 4-(4-chlorophenyl)cyclohexane carboxylic acid.

In another embodiment, the present invention provides atovaquone in a substantially pure polymorphic form, hereinafter referred to as new compound of the invention. The compound of the invention is characterized by the positions of the major peaks in the X-ray powder diffractogram, but may also be characterized by FT-IR spectroscopy and endotherms in DSC diagram. These characteristics are not exhibited by any other form of atovaquone and accordingly, Form IPCA-ATO of the present invention is easily distinguishable from any other crystal form of the atovaquone disclosed in prior art.

Figure 2:
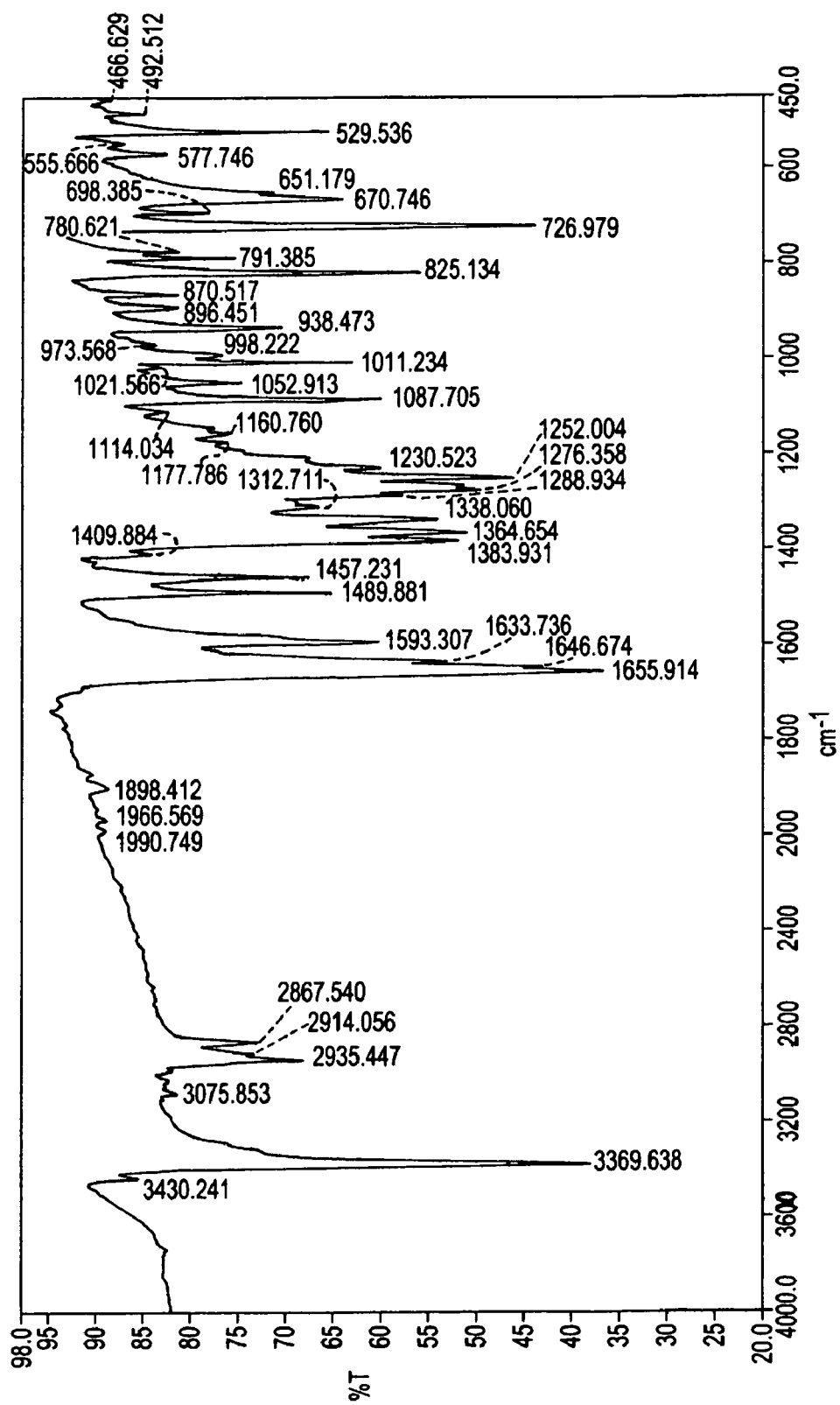
FIG. 2 shows an IR spectra of "Form IPCA-ATO" of atovaquone obtained in accordance with the invention.

Thus, the character of this new form (Form IPCA-ATO) is confirmed either by PXRD patterns, DSC endotherms, or FT IR spectra obtained from a sample thereof which are provided in FIGS. 1 to 3. The PXRD pattern shows at least one characteristic or exclusive peak at about 6.66 and 9.96±0.2 degrees 2 theta angles. More particularly, the PXRD pattern shows characteristic and exclusive peaks at 6.66, 9.96, 13.11, 18.22, and 23.03±0.2 degrees 2θ angles.

The novel form of atovaquone "Form IPCA-ATO" is further characterized by FT-IR spectra having peaks at 3369, 2935, 1633, 1383, 1338, 1312, 1231 and 1053 $cm^{-1}$, which are characteristic for the present form.

The novel form of atovaquone (Form IPCA-ATO) is further characterized by endotherms in a DSC. Thermal analysis results in a Differential Scanning calorimeter thermogram taken at a heating rate of 10° C. per minute in an open pan that exhibits a melting endotherm with a peak temperature of about 117-130° C. (an onset temperature in the range of about 100-120° C.), and a second endotherm having peak at about 220-222° C. (onset temperature in the range of about 217-219). The position of the first endotherm can shift the position depending upon the heating rate and any contaminations.

The main XRPD peaks, with positions and relative intensities, have been extracted from the diffractogram in FIG. 1 and are given below in table 1. The relative intensities are less reliable and some additional very weak peaks found in the diffractogram have been omitted from table 1.

TABLE 1

| 2θ values in degrees | d spacing | Percentage relative intensity |
|---|---|---|
| 6.66 | 13.42 | 30.06 |
| 9.96 | 8.8 | 12.58 |
| 13.11 | 6.7 | 6.36 |
| 18.22 | 4.8 | 100.00 |
| 23.03 | 3.8 | 28.93 |
| 32.90 | 2.7 | 4.87 |

In a further aspect, the present invention provides processes for the preparation of the atovaquone Form IPCA-ATO which comprises; i) contacting atovaquone of any physical form in an organic solvent to obtain a solution at a suitable temperature for a suitable time; ii) subjecting it to rapid chilling; and iii) recovering the novel form from the reaction solution.

In one embodiment of the present invention, preparation of Form IPCA-ATO of atovaquone comprises i) subjecting a solution of atovaquone to chilling either in a cold bath of liquid nitrogen or dry ice bath prepared in a suitable solvent medium until frozen and removing the solvent from the mass thus obtained to recover the new crystals of atovaquone. Alternately the atovaquone solution may be added to either liquid nitrogen or dry ice to precipitate the new form followed by removal of the solvent. The solvent may be removed under vacuum, preferably in a lyophilizer. The organic solvents may be selected from, but are not limited to, chlorinated solvents, especially dichloromethane.

"Suitable temperature" means a temperature at which the solution can be formed and be able to induce the transformation of atovaquone into the novel form. Examples of such suitable temperatures include, but are not limited to, room temperature or lower, preferably less than 0° C., and more preferably less than minus 30° C.

"Suitable time" means a time that results in better conversion of the starting material into novel crystalline form without causing any decomposition of either compounds, i.e. results in a good yield. This suitable time will vary depending on the mode of chilling used and can be established by routine experimentation. The faster the rate of cooling, the shorter time is needed to give the desired conversion. The amount of solvent is not crucial and will depend on the process conversion and conditions desired. To have complete conversion to the novel form of the present invention, complete dissolution of atovaquone in the selected solvent is desired. The process conditions are further illustrated in the non-limiting Examples.

Atovaquone has been indicated for use for the following indications: *Pneumocystis carinii*, Plasmodia, and tachyzoite and cyst forms of *Toxoplasma gondii*. It may be used alone or concomitantly with other classes of agents like mefloquine or proguanil (Anti-malarials).

In a further aspect, the invention provides a new compound which is atovaquone Form IPCA-ATO for use in treating *Pneumocystis carinii*, Plasmodia, and tachyzoite and cyst forms of *Toxoplasma gondii*, either alone or in combination with other anti-malarial agents. In the practice of the invention, the most suitable route of administration as well as the magnitude of a therapeutic dose of atovaquone Form IPCA-ATO in any given case will depend on the nature and severity of the disease to be treated. The dosage and dose frequency may also vary according to the age, body weight and response of the individual patient.

The invention thus provides pharmaceutical compositions containing atovaquone Form IPCA-ATO which may optionally contain other crystalline forms and/or other active pharmaceutical drugs. In addition to the active ingredient(s), the pharmaceutical compositions of the present invention can contain one or more commonly used pharmaceutical excipients which are added to the composition for a variety of purposes known in the art.

The bulk density of the new form was compared with the crystalline forms and found that the new form is lighter than other forms, the results are summarized in the below table.

| Ser. No. | Sample name | Bulk density g/ml | Tapped density g/ml |
|---|---|---|---|
| 1 | Form I (ATO-8094P) | 0.4802 | 0.6402 |
| 2 | Form III(ATO-8110) | 0.2975 | 0.4010 |
| 3 | Form IPCA-ATO (ATO-8099) | 0.2353 | 0.3801 |

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in these examples.

Example 1

Preparation of 2-[4-(4-chlorophenyl)cyclohexyl]-1,4-naphthoquinone (Formula II)

To a stirred solution of silver nitrate (17.5 g, 0.104 moles) dissolved in 100 ml water, 50 g (0.209 moles) trans-4-(4-chlorophenyl)cyclohexane carboxylic acid was added. To this solution acetonitrile (250 ml) was added and under stirring and heated to reflux. 33.1 g (0.209 moles) 1,4-naphthoquinone was then added. 120 g (0.525 mole) ammonium persulfate dissolved in 400 ml water was added drop-wise to the stirred solution and continued reflux for 2 hours. The reaction solution was then cooled to 0-5° C. and extracted with methylene chloride. The organic layer was first washed with water, followed by 10% sodium carbonate aqueous solution, and further with water until the pH is neutral. The organic layer was distilled to eliminate methylene chloride and was then stirred in acetonitrile and filtered. The solid obtained was crystallized from acetonitrile to obtain 15 g of trans-2-[4-(4-chlorophenyl)cyclohexyl]-1,4-naphthoquinone (20% yield). M.P. 146-149 (uncorrected), $^1$H NMR (400 MHz), $\delta$H ($d_6$-CDCl3) 8.07-8.14 (2H, m, Naphth), 7.65-7.74 (2H, m, Naphth), 7.27-7.30 (2H, d, arom.), 7.07-7.19 (2H, d, arom.), 6.80 (1H, s, naphtho.), 2.98-3.01 (1H, tt, CH), 2.54-2.58 (1H, tt, CH—), 1.25-2.03 (8H, multi, $CH_2$).

Example 2

Preparation of 2-[4-(4-chlorophenyl)cyclohexyl]-2,3-dichloro-2,3-dihydro-1,4-naphthoquinone (Formula III)

10 g of the compound of Formula II (2-[4-(4-chlorophenyl)cyclohexyl]-1,4-naphthoquinone) as obtained in Example 1 was added to 50 ml glacial acetic acid. Chlorine gas was passed into this solution at about 20° C. The reaction mass was then quenched in water and filtered. The product was dried at 30° C. to obtain 11.5 g of the compound of formula III (95% yield) of the compound of Formula III. $^1$H NMR (400 MHz), $\delta$H ($d_6$-CDCl$_3$) 8.13 (2H, m, Naphth), 7.82-7.89 (2H, m, Naphth), 7.0-7.30 (4H, m, arom.), 4.90-5.0 (1H), 2.67 (1H, tt, CH), 2.49 (1H, m, CH—), 1.2-2.0 (8H, multi, $CH_2$)

Example 3

Preparation of trans-2-[4-(4-chlorophenyl)cyclohexyl]-3-chloro-1,4-naphthoquinone (trans-Formula IV)

10 g of 2-[4-(4-chlorophenyl)cyclohexyl]-2,3-dichloro-2,3-dihydro-1,4-naphthoquinone (Formula III) obtained in example 2 was suspended in glacial acetic acid (80 ml). 2.9 g of anhydrous sodium acetate was added to the mixture and heated to reflux for 1 hour and then cooled. Water was then added to the mixture. The precipitated product was filtered of and recrystallized from acetonitrile to obtain 6.5 g (70% yield) of the trans isomer of the compound of Formula IV.

Example 4

Preparation of Atovaquone 6.0 g of trans-2-[4-(4-chlorophenyl)cyclohexyl]-3-chloro-1,4-naphthoquinone (trans-isomer of Formula IV) as obtained in Example 3 was suspended in 120 ml methanol. 6.0 g sodium hydroxide dissolved in 60 ml water was added drop-wise to the suspension under heating over a period of 20 minutes. Further, it was refluxed for 45 minutes and cooled to 0-5° C. and filtered. The filtrate was acidified with 50% aqueous hydrochloric acid to precipitate the product. The precipitated product was filtered, and recrystallized from acetonitrile to obtain 4 g (70% yield) atovaquone.

Example 5

Preparation of 2-[4-(4-chlorophenyl)cyclohexyl]-1,4-naphthoquinone (Formula II)

A mixture of 14.17 g silver nitrate (0.0838 moles) in 200 ml water, and 100 g (0.419 moles) trans-4-(4-chlorophenyl)cyclohexane carboxylic acid were prepared. To this mixture acetonitrile 500 ml was added under stirring and heated to reflux. 80 g (0.506 moles) 1,4-naphthoquinone was then added. 239 g (1.048 moles) ammonium persulfate dissolved in 600 ml water was added drop-wise to the stirred solution and continued reflux for half an hour. The reaction solution was then cooled to 30-32° C. and extracted with methylene chloride. The organic layer was first washed with water, followed with 10% sodium carbonate aqueous solution, and further with water until neutral pH. The organic layer was distilled to eliminate methylene chloride, stirred in acetonitrile, and filtered. The solid obtained was crystallized from acetonitrile to obtain 29.8 g of the trans isomer of Formula II (20.3% yield). M.P. 147- 149° C. (uncorrected).

Example 6

Preparation of 2-[4-(4-chlorophenyl)cyclohexyl]-2,3-dichloro-2,3-dihydro-1,4-naphthoquinone (Formula III)

117 g of compound of Formula II (2-[4-(4-chlorophenyl)cyclohexyl]-1,4-naphthoquinone) as obtained in Example 5 was added to 585 ml glacial acetic acid. Chlorine gas was then passed through this solution at about 15° C. The reaction mass was filtered, and washed with glacial acetic acid and water. The product was dried at 30° C. to obtain 120 g (85% yield) of compound of Formula III.

Example 7

Preparation of trans-2-[4-(4-chlorophenyl)cyclohexyl]-3-chloro-1,4-naphthoquinone (trans-Formula IV)

115.8 g of 2-[4-(4-chlorophenyl)cyclohexyl]-2,3-dichloro-2,3-dihydro-1,4-naphthoquinone (Formula III) obtained in Example 6 was suspended in glacial acetic acid (926 ml). 33.77 g anhydrous sodium acetate was then added to the mixture and heated to reflux for 1 hour. After which, the mixture was cooled. Water was then added. The precipitated product was filtered of and recrystallized from acetonitrile to obtain 94.5 g (89.34% yield) of the trans-isomer of the compound of Formula IV.

Example 8

Preparation of Atovaquone 87.3 g of trans-2-[4-(4-chlorophenyl)cyclohexyl]-3-chloro-1,4-naphthoquinone (trans-isomer of Formula IV) as obtained in Example 7 was suspended in 2619 ml methanol. 128 g potassium hydroxide was dissolved in 873 ml water and added drop-wise to the suspension under heating over a period of 20 minutes. Refluxed was extended for another 45 minutes before cooling to 0-5° C. and filtered. The filtrate was acidified with 50% aqueous hydrochloric acid to precipitate the product. The precipitated product was filtered, and recrystallized from acetonitrile to obtain 71.6 g (86% yield) atovaquone.

Example 9

Preparation of Atovaquone Form IPCA-ATO 1.0 grams of atovaquone (Form I) was taken in 35 ml of dichloromethane at room temperature. It was dissolved completely and filtered out any undissolved particles. The solution was then chilled on a nitrogen bath until the dichloromethane solution solidified. The material was lyophilized and dichloromethane was removed completely to obtain the novel crystalline form. Yield 1.0 g. The XRPD, IR spectra and DSC of the sample were consistent with those depicted in FIGS. 1 to 3.

Example 10

Preparation of Atovaquone Form IPCA-ATO 1.0 grams of atovaquone (Form I) was taken in 35 ml of dichloromethane at room temperature. It was dissolved completely and filtered out of any undissolved particles. The solution was poured on liquid nitrogen taken in another vessel until the dichloromethane solution solidified. The solid obtained was lyophilized and dichloromethane was removed completely to obtain the novel crystalline form. Yield 1.0 g. The XRPD, IR spectra and DSC of the sample were consistent with those depicted in FIGS. 1 to 3.

Example 11

Preparation of Atovaquone

To a solution of silver nitrate (14.17 g, 0.0838 moles) dissolved in 200 ml water, 100 gm (0.419 moles) trans-4-(4-chlorophenyl)cyclohexane carboxylic acid and acetonitrile (500 ml) was added. The solution was heated to reflux followed by addition of 1,4-naphthoquinone (80 gm, 0.506 moles). A solution of ammonium persulfate (239 g; 1.048 moles) in water (600 ml) was added dropwise to the above solution and continued reflux for half an hour. The reaction mass was then cooled to 30-32° C. and extracted with methylene chloride. The organic layer was first washed with water, followed with 10% sodium carbonate aqueous solution, and further with water until neutral pH. The organic layer was concentrated to afford the compound of Formula II (2-[4-(4-chlorophenyl)cyclohexyl]-1,4-naphthoquinone, 149 gm).

The compound of Formula II obtained was added to glacial acetic acid (745 ml). To this solution, chlorine gas was passed at about 20° C. After the complete disappearance of the starting material, nitrogen gas was purged to remove excess chlorine from the reaction mass. Anhydrous sodium acetate (52.3 gm) was then added and the reaction mass and was heated to reflux for 90 minutes. The reaction mass was cooled and quenched into a mixture of methylenechloride and water. The methylenechloride was washed with water until neutral pH. The solvent is concentrated to obtain residue containing the compound of Formula IV (155 gm).

The residue obtained (Formula IV) was suspended in 4.5 liter methanol. A solution of potassium hydroxide (225 gm) in water (1550 ml) was added drop-wise under heating over a period of one hour. The reaction mass was then refluxed for 2 hours and cooled to 30-32° C. and filtered. The filtrate was neutralized with 50% aqueous hydrochloric acid to precipitate atovaquone in a cis/trans-isomeric mixture (116 gm).

Example 12

Epimerization

The cis/trans isomeric mixture (116 gm) obtained in Example 11 was added to 1100 ml of 90% sulphuric acid and stirred at 28-30° C. The reaction was monitored by HPLC, when the cis isomer was less than 0.5%, the reaction mixture was quenched into ice-water, filtered, washed with water till neutral pH. The crude product was purified in acetonitrile and methylenedichloride to obtain atovaquone (trans-isomer) (44 gm). Yield: 28.5%. HPLC purity: 99.8%

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A compound of Formula III

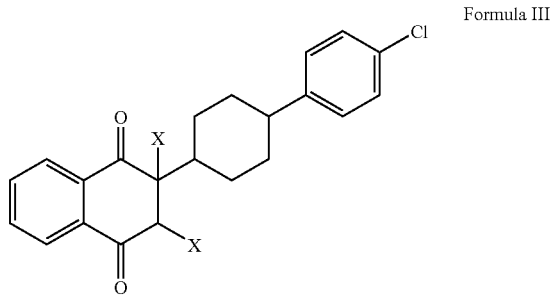

Formula III where X is a halogen.

2. The compound of claim 1, wherein the halogen is chlorine.

3. A trans-compound of Formula II

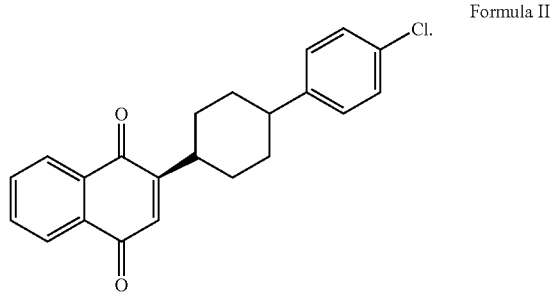

Formula II

4. A process for making the compound of claim 3 comprising the step of reacting a compound of Formula V with a compound of Formula VI Formula V

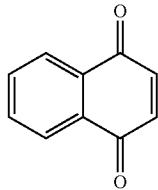

Formula VI

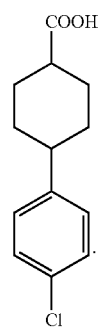

5. The process of claim 4, wherein the reacting step is in the presence of a metal nitrate and persulfate compound.

6. The process of claim 4, wherein the reacting step is in the presence of silver nitrate and ammonium persulphate.

7. A process for making the compound of claim 1 comprising the steps of:
   a) reacting a compound of Formula V with a compound of Formula VI to obtain a compound of Formula II; and Formula V

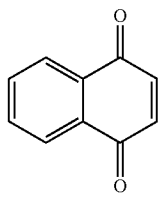

Formula VI

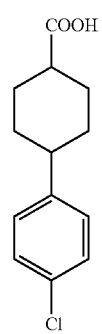

Formula II

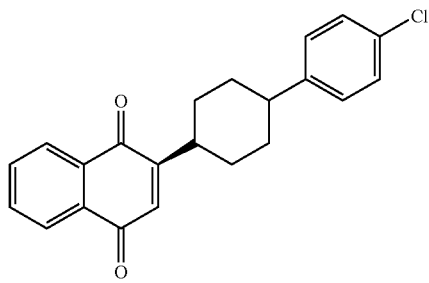

b) reacting the compound of Formula II with a halogenating agent.

8. The process according to claim 7, wherein step a) is carried out in presence of a metal nitrate and persulphate compound.

9. The process according to claim 7, wherein the step a) is carried out in presence of silver nitrate and ammonium persulphate.

10. The process according to claim 7, wherein the halogenating agent is chlorine.

11. A process for making atovaquone of Formula I or its cis-isomer or an isomeric mixture thereof Formula I

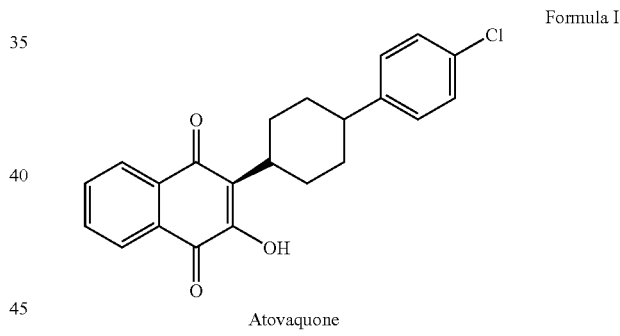

Atovaquone comprising the step of converting a compound of Formula III

Formula III

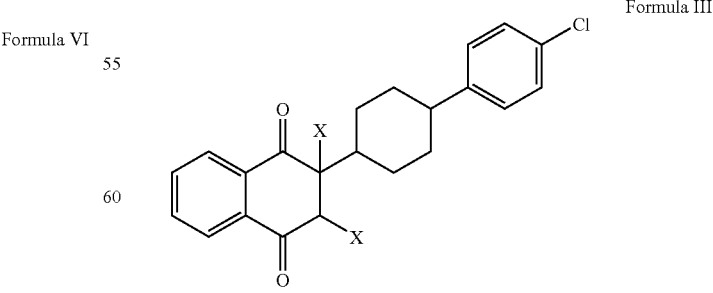

to atovaquone or its cis-isomer, where X is a halogen.

12. The process of claim 11, wherein the converting step comprises:
   a) dehydrohalogenating the compound of Formula III to obtain a compound of Formula IV Formula IV

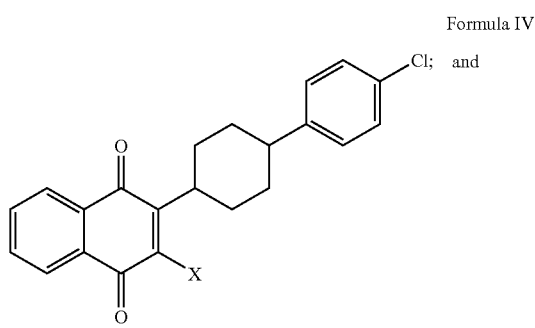

b) converting the compound of Formula IV to atovaquone.

13. The process of claim 12, wherein step a) is carried out in presence of sodium acetate.

14. The process of claim 11, wherein the compound of Formula III is obtained by reacting a compound of Formula II Formula II with a halogenating agent.

15. The process of claim 14, wherein the halogenating agent is chlorine.

16. The process of claim 11, further comprising the step of epimerizing the cis-isomer or the isomeric mixture to atovaquone.

17. A process for making trans-2-[4-(4-chlorophenyl)cyclohexyl]-3-hydroxy-1,4-naphthoquinone (atovaquone) comprising the steps of:

a) dehydrohalogenating a compound of Formula III to obtain a compound of Formula IV Formula III Formula IV wherein X is a halogen, and the compound of Formula IV is a cis isomer or a trans isomer or a mixture of cis and trans isomers; and b) converting the compound of Formula IV into 2-[4-(4-chlorophenyl)cyclohexyl]-3-hydroxy-1,4-naphthoquinone, wherein the 2-[4-(4-chlorophenyl)cyclohexyl]-3-hydroxy-1,4-naphthoquinone is a cis isomer or trans isomer or a mixture of cis and trans isomers.

18. The process of claim 17, wherein step a) is carried out in the presence of sodium acetate.

19. The process of claim 17, wherein in step b) the compound of Formula IV is hydrolyzed to 2-[4-(4-chlorophenyl)cyclohexyl]-3-hydroxy-1,4-naphthoquinone.

20. The process of claim 17, further comprising the step of epimerizing the 2-[4-(4-chlorophenyl)cyclohexyl]-3-hydroxy-1,4-naphthoquinone produced in step b) to obtain trans-2-[4-(4-chlorophenyl)cyclohexyl]-3-hydroxy-1,4-naphthoquinone (atovaquone).

21. The process of claim 20, wherein the epimerizing step is carried out in presence of sulfuric acid.

* * * * *